United States Patent
Ben-Zion et al.

(10) Patent No.: US 9,791,367 B2
(45) Date of Patent: Oct. 17, 2017

(54) HYBRID FIBER OPTIC PROBE DEVICE FOR ATTENUATED TOTAL REFLECTION SPECTROSCOPIC APPLICATIONS IN UV, VISIBLE AND IR RANGES

(71) Applicant: PIMS PASSIVE IMAGING MEDICAL SYSTEMS LTD, Emek Hefer (IL)

(72) Inventors: Dekel Ben-Zion, Hadera (IL); Arkadi Zilberman, Beer Sheeba (IL); Ronnie Klein, Haifa (IL); Yaniv Cohen, Jerusalem (IL); Nathan Blaunstein, Beer Sheeba (IL)

(73) Assignee: PIMS PASSIVE IMAGING MEDICAL SYSTEMS LTD, Be'er Sheva (IL)

( * ) Notice: Subject to any disclaimer, the term of this patent is extended or adjusted under 35 U.S.C. 154(b) by 202 days.

(21) Appl. No.: 14/895,494
(22) PCT Filed: Jun. 3, 2014
(86) PCT No.: PCT/IL2014/050504
§ 371 (c)(1),
(2) Date: Dec. 3, 2015
(87) PCT Pub. No.: WO2014/195949
PCT Pub. Date: Dec. 11, 2014

(65) Prior Publication Data
US 2016/0116407 A1    Apr. 28, 2016

Related U.S. Application Data

(60) Provisional application No. 61/830,651, filed on Jun. 4, 2013.

(51) Int. Cl.
*G02B 6/02*     (2006.01)
*G01N 21/552*   (2014.01)
(Continued)

(52) U.S. Cl.
CPC ....... *G01N 21/552* (2013.01); *G01N 21/8507* (2013.01); *G02B 6/02328* (2013.01);
(Continued)

(58) Field of Classification Search
None
See application file for complete search history.

(56) References Cited

U.S. PATENT DOCUMENTS

| | | | |
|---|---|---|---|
| 4,830,462 | A | 5/1989 | Karny et al. |
| 5,436,454 | A | 7/1995 | Bornstein et al. |

(Continued)

FOREIGN PATENT DOCUMENTS

| | | |
|---|---|---|
| DE | 4038354 A1 | 6/1992 |
| DE | 4414975 A1 | 11/1995 |

OTHER PUBLICATIONS

Heise H M et al: "Attenuated Total Reflection MI-Infrared Spectroscopy for Clinical Chemistry Applications Using Silver Halide Fibers" Sensors and Actuators B: Chemical: International Journal Devoted to Research and Ddevelopment of Physical and Chemical Transducers, Elsevier BCV, NL, vol. 51, No. 1-3.

*Primary Examiner* — Jerry Rahll
(74) *Attorney, Agent, or Firm* — Mark M. Friedman

(57) ABSTRACT

A hybrid Attenuated Total Reflection fiber optic probe device having a radiation source; a detecting system; a core-only solid optical fiber probe tip having an input end and an output end; an input hollow fiber waveguide configured for association with the radiation source at a first end and interconnection with the input end of the core-only solid optical fiber probe tip at a second end; an output hollow fiber waveguide configured for interconnection with the output end of the core-only solid optical fiber probe tip at a first end and association with the detection system at a second end; an inwardly tapered solid fiber input radiation collector element configured at a tapered end for interconnection with the second end of the output hollow fiber waveguide so as to receive radiation from the radiation source; wherein an outside diameter of the core-only solid optical fiber probe tip and an inside diameter of each one of the input hollow fiber waveguide and the output hollow fiber waveguide is such that the interconnection between each one of the input hollow fiber waveguide and the output hollow fiber waveguide and the core-only solid optical fiber probe tip is by means of inserting the input end of the core-only solid optical fiber probe tip into the second end of the input hollow fiber waveguide and inserting the output end of the core-only solid optical fiber probe tip into the first end of the output hollow fiber waveguide, such that the core-only solid optical fiber probe tip is held in the input and output hollow (Continued)

fiber waveguides by means of friction, and wherein an outside diameter of a portion of the inwardly tapered solid fiber input radiation collector element and an inside diameter of the second end of the output hollow fiber waveguide is such that the tapered end of the inwardly tapered solid fiber input radiation collector element is held in the end of the second end of the output hollow fiber waveguide by means of friction.

10 Claims, 7 Drawing Sheets

(51) Int. Cl.
*G01N 21/85* (2006.01)
*G02B 6/26* (2006.01)
*C03C 25/10* (2006.01)
*G02B 6/032* (2006.01)

(52) U.S. Cl.
CPC ...... *C03C 25/10* (2013.01); *G01N 2021/8542* (2013.01); *G02B 6/032* (2013.01); *G02B 6/262* (2013.01)

(56) References Cited

U.S. PATENT DOCUMENTS

| | | |
|---|---|---|
| 5,585,634 A | 12/1996 | Stevenson et al. |
| 5,926,269 A | 7/1999 | Von Der Eltz et al. |
| 6,104,853 A | 8/2000 | Miyagi et al. |
| 6,122,041 A | 9/2000 | Najm et al. |
| 6,200,502 B1 | 3/2001 | Paatzsch et al. |
| 7,763,009 B1 | 7/2010 | Weiss |
| 2005/0046807 A1 | 3/2005 | Hanano |
| 2006/0153502 A1 | 7/2006 | Giotto et al. |
| 2006/0285797 A1 | 12/2006 | Little |
| 2011/0170116 A1 | 7/2011 | Homa et al. |

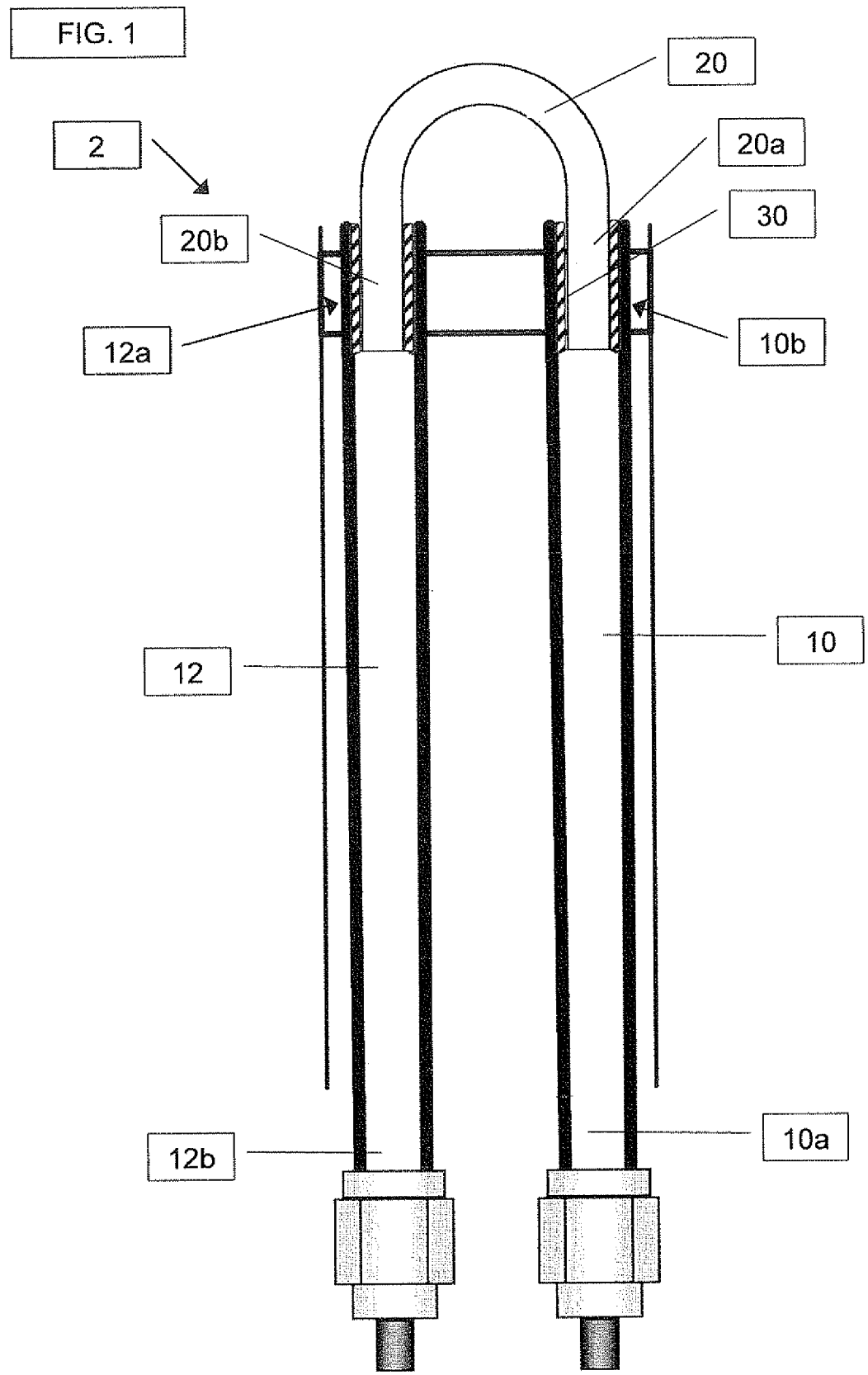

102  104  106f 102  104  106r

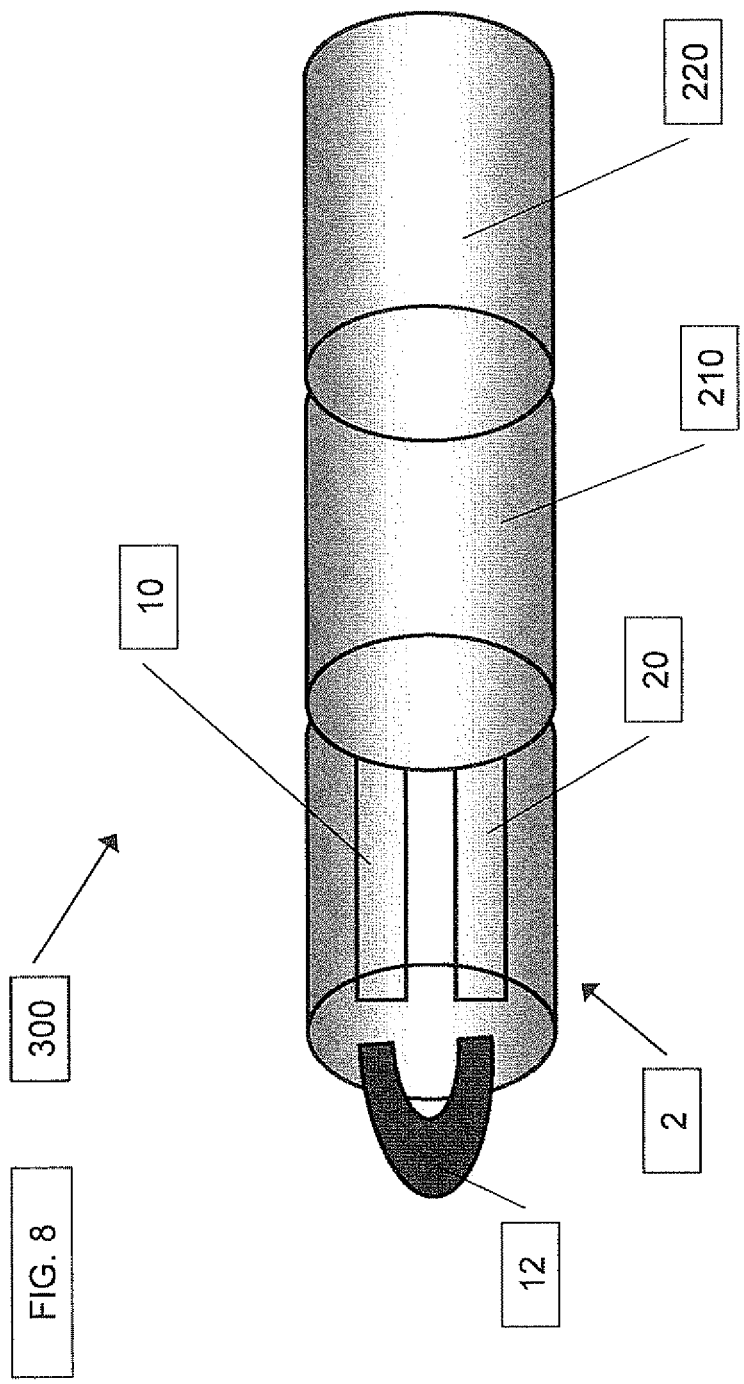

HYBRID FIBER OPTIC PROBE DEVICE FOR ATTENUATED TOTAL REFLECTION SPECTROSCOPIC APPLICATIONS IN UV, VISIBLE AND IR RANGES

FIELD AND BACKGROUND OF THE INVENTION

The present invention relates to fiber optic probes for use in spectroscopic applications in general and, in particular, it concerns a hybrid. Attenuated Total Reflection (ATR) fiber optic probe device. Additionally, it concerns a method for attaching a solid optical fiber core tip to hollow fiber waveguides.

More specifically, the present invention relates to a probe device and innovative accessories used in conjunction with a detecting system such as, but not limited to, a spectrophotometer or a spectrometer. The probe device of the present invention is especially well suited for use with Fourier Transform spectrometers. The accessories utilize transmitting optical waveguides, radiation sources, opto-mechanical components (reflectors, etc.) to enable spectral analysis of samples remotely from the detector or measuring system using Attenuated Total Reflectance (ATR).

It is an object of the invention to provide a hybrid fiber optic probe for spectroscopic ATR applications that has high efficiency over a wide range of wavelengths (UV, VIS, IR). In certain embodiments it can have a small diameter and have high flexibility.

Fiber optic probes for spectroscopic applications are well known and have long been used to measure the properties of samples at different states.

In general, and especially in medical applications, such fiber optic probe comprises a first fiber or a first bundle of fibers to guide radiation from the proximal end of the probe to the distal end of the probe, and a second fiber or second bundle of fibers are used to guide radiation back to the proximal end of the probe.

An optical element such as an Attenuated Total Reflectance (ATR) head or tip is arranged at the distal end of the fiber probe. The optical element generally is arranged and adapted in a way that it interacts with a sample, such as biological tissue, for determining the spectroscopic properties (spectral signatures) of the sample. In doing so, radiation emitted by the ATR element is modified by the sample, reenters the ATR element and is reflected back into the optical fiber or the bundle of the optical fibers. The reflected light eventually is emitted from the proximal end of the fiber and can be received by a detecting system such as a spectrometer based on diffraction grating, Fourier Transform spectrometer/interferometer or spectral filter with a related photo-element or array of detectors.

The ATR crystals that are remotely linked to detecting system (e.g., FTIR spectrometers) by way of fiber optics are widely used in spectroscopic applications. Single-fiber systems (systems using one input and one output optical fiber) are commonly used and generally include complex coupling means to transfer radiation from the optical fiber into the ATR crystal and back again.

ATR spectrometry is used extensively in clinical assays, medical diagnostics, and lab testing.

Examples of such ATR fiber optic probes are disclosed in U.S. Pat. Nos. 5,754,722, 7,956,317, 6,879,741, 6,563,992, 4,930,863, 6,841,792, 5,170,056, 6,970,623, 5,185,834, 5,070,243.

The ATR technique makes use of the fact that, pursuant to Snell's Law, when the beam of light impinges on the interface between the first and second medium at or above a critical angle, defined as $\theta crit=sin-1 n2/n1$ (where n1, n2 are the refractive indexes of first and second medium respectively), there is no refracted ray, i.e., the incident light is totally internally reflected, and an evanescent wave is generated. "Evanescent" means "tending to vanish," which is appropriate because the intensity of evanescent waves decays exponentially with distance from the interface at which they are formed. This distance is typically in the 1-50 um range. As a result the intensity of the reflected light is reduced at those wavelengths at which the surrounding medium absorbs.

In AIR spectrometry, a sample is measured by passing radiation through an optical element (crystal), which can be mounted on a probe. The radiation, which for example can be UV, Vis, or IR, is directed onto the optical element at an angle of incidence such that all incident radiation undergoes total internal reflection. When the radiation undergoes total internal reflection, an electro-magnetic radiation field (evanescent wave) extends beyond the surface of the optical element into the sample. The depth of penetration of the evanescent wave is a function of the refractive index of the optical element material, refractive index of the sample material, angle of incidence of the radiation wavefront, and wavelength of the radiation. In regions of the spectrum where the sample absorbs energy, the evanescent wave is attenuated and the attenuated energy is passed back to the optical element. The radiation then exits the optical element and impinges a detector through optical waveguide/fiber. The detector records the attenuated radiation, which can then be transformed to generate a spectrum, e.g., absorption spectra.

An ATR spectrum is generated by transmitting radiation, which can be IR (from about ~0.75 um to ~0.1 mm), VIS (~0.35 um to ~0.75), or UV (from ~0.22 um to ~0.35 um), through an optical crystal (element) in contact with a sample and then determining what portion of the incident radiation is attenuated by the sample at a particular wavelength.

The spectrum of the transmission losses is the basis of attenuated total reflectance (ATR) spectroscopy.

There is therefore a need for a hybrid Attenuated Total Reflection (ATR) fiber optic probe device. Additionally, there is a need for a method for attaching a solid optical fiber core tip to hollow fiber waveguides.

SUMMARY OF THE INVENTION

The present invention is a hybrid. Attenuated Total Reflection (ATR) fiber optic probe device. Additionally, it includes a method for attaching a solid optical fiber core tip to hollow fiber waveguides.

According to the teachings of the present invention there is provided, a hybrid Attenuated Total Reflection fiber optic probe device comprising: (a) a radiation source; a detecting system; a core-only solid optical fiber probe tip having an input end and an output end; an input hollow fiber waveguide configured for association with the radiation source at a first end and interconnection with the input end of the core-only solid optical fiber probe tip at a second end; an output hollow fiber waveguide configured for interconnection with the output end of the core-only solid optical fiber probe tip at a first end and association with the detection system at a second end; an inwardly tapered solid fiber input radiation collector element configured at a tapered end for interconnection with the second end of the output hollow fiber waveguide so as to receive radiation from the radiation source; wherein an outside diameter of the core-only solid optical fiber probe tip and an inside diameter of each one of the input hollow fiber waveguide and the output hollow fiber waveguide is such that the interconnection between each one of the input hollow fiber waveguide and the output hollow fiber waveguide and the core-only solid optical fiber probe tip is by means of inserting the input end of the core-only solid optical fiber probe tip into the second end of the input hollow fiber waveguide and inserting the output end of the core-only solid optical fiber probe tip into the first end of the output hollow fiber waveguide, such that the core-only solid optical fiber probe tip is held in the input and output hollow fiber waveguides by means of friction, and wherein an outside diameter of a portion of the inwardly tapered solid fiber input radiation collector element and an inside diameter of the second end of the output hollow fiber waveguide is such that the tapered end of the inwardly tapered solid fiber input radiation collector element is held in the end of the second end of the output hollow fiber waveguide by means of friction.

According to the teachings of the present invention the interconnection between the core-only solid optical fiber probe tip and the input and output hollow fiber waveguides is a releasable interconnection.

According to the teachings of the present invention the interconnection between the core-only solid optical fiber probe tip and the input and output hollow fiber waveguides includes a layer of a noble metal on a surface area of contact between the core-only solid optical fiber probe tip and the input and output hollow fiber waveguides.

There is also provided according to the teaching of the present invention an inwardly tapered solid fiber input radiation collector element for receiving radiation from a radiation source and transmitting the radiation into a hollow fiber waveguide, the inwardly tapered solid fiber input radiation collector element comprising: an input face; an inwardly tapered section extending from the input face to; a output connection section configured for interconnection with the hollow fiber waveguide and having a substantially constant diameter that is smaller than a diameter of the input face; wherein the diameter of the connection section and an inside diameter of the hollow fiber waveguide is such that the inwardly tapered solid fiber input radiation collector element is held in the end of the hollow fiber waveguide by means of friction.

According to the teachings of the present invention the input face is flat.

According to the teachings of the present invention the input face is lens shaped.

There is also provided according to the teaching of the present invention a method for attaching a solid optical fiber element to a hollow fiber waveguide, the method comprising: providing a solid optical fiber element having at least one of an input end and an output end; providing at least one hollow fiber waveguide configured for interconnection with one of the input end and output end of the solid optical fiber element at an end; and inserting at least one of the input end and an output end at least partially into the end of the hollow fiber waveguide; wherein an outside diameter of the solid optical fiber element and an inside diameter of the hollow fiber waveguide is such that the solid optical fiber element is held in the end of the hollow fiber waveguide by means of friction.

According to the teachings of the present invention the solid optical fiber element is implemented as a core-only solid optical fiber probe tip having an input end and an output end, the at least one hollow fiber waveguide is implemented as two hollow fiber waveguides configured as an input hollow fiber waveguide and an output hollow fiber waveguide and the inserting includes inserting the input end of the core-only solid optical fiber probe tip at least partially into the input hollow fiber waveguide and inserting the output end of the core-only solid optical fiber probe tip at least partially into the output hollow fiber waveguide.

According to the teachings of the present invention the solid optical fiber element is implemented as an inwardly tapered solid fiber input radiation collector element having at least an output connection section.

According to the teachings of the present invention, there is also provided coating a surface area of contact between the solid optical fiber element and the at least one hollow fiber waveguide with a layer of a noble metal.

BRIEF DESCRIPTION OF THE DRAWINGS

The invention is herein described, by way of example only, with reference to the accompanying drawings, wherein:

FIG. 1 is a side section of a preferred embodiment of a hybrid Attenuated Total Reflection (ATR) fiber optic probe device constructed and operational according to the teaching of the present invention;

FIG. 8 is a block diagram of a miniaturized probe system incorporating a hybrid ATR fiber optic probe device of the present invention.

DESCRIPTION OF THE PREFERRED EMBODIMENTS

Figure 2A:
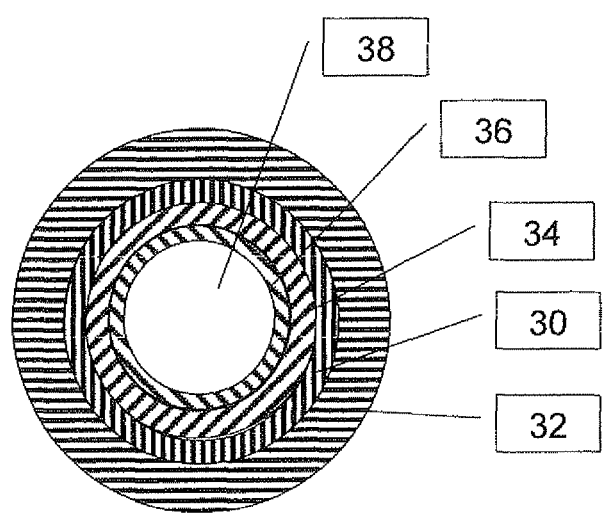
FIGS. 2A and 2B are top and side elevations, respectively, of the hollow fiber waveguide of FIG. 1.

The present invention is a hybrid Attenuated Total Reflection (ATR) fiber optic probe device. Additionally, a method for attaching a solid optical fiber core tip to hollow fiber waveguides The principles and operation of a hybrid Attenuated Total Reflection (ATR) fiber optic probe device and a method for attaching a solid optical fiber core tip to hollow fiber waveguides according to the present invention may be better understood with reference to the drawings and the accompanying description.

By way of introduction, it is an object of the present invention to provide a convenient means for obtaining spectra from samples in a variety of physical forms and states, using an assembly which comprises a hybrid fiber optic probe to transfer the radiation from a source to the sample and from the sample to the detector.

The hybrid ATR fiber optic probe of the present invention is particularly appropriate for facilitating the determination of spectra (spectral signatures) in biological tissues, solid materials, liquids, aqueous solutions, gels, mud, creams, pastes, oils and suspensions, and the like and can be used in various applications for determination of spectroscopic signatures including medical, pharmaceutical and environmental such as, but not limited to, monitoring water quality.

The spectral signature is obtained from the sample by means of Attenuated Total Reflection (ATR), using interchangeable ATR heads/tips.

To create the ATR element, the cladding of the optical fiber is removed and the core is placed in direct contact with the sample. When light experiences total internal reflection at the core-sample interface, some of the energy of the light waves in the core of the fiber penetrate into the sample for a very short distance. The energy flow of this evanescent wave is parallel to the surface of the core and in the same direction as the main flow of energy within the core; therefore, any materials which absorb the particular wavelength of radiation will take energy out of the evanescent wave.

The hybrid ATR probe is operative in the wide region of the electromagnetic spectrum such as, but not limited to, UV, VIS and IR for in situ sensing of the absorption of radiation in a sample.

With the proposed coupling arrangement the need to use large size optical elements (like expensive Diamond ATR elements) is eliminated. As a result, the probe diameter can be substantially reduced together with the price, while the resulting probe will be more flexible and can be used, for example, for endoscopy.

Referring now to the drawings, FIG. 1 illustrates a preferred embodiment of an ATR probe 2 having a core-only solid optical fiber probe tip 20 attached to an input hollow fiber waveguide 10 and an output hollow fiber waveguide 12. It will be understood the radiation is introduced into and travels through the input hollow fiber waveguide 10, enters and travels through the core-only solid optical fiber probe tip 20 and then enters and travels through the output hollow fiber waveguide 12 Therefore, input hollow fiber waveguide 10 is configured with an input end 10a for receiving radiation and an output end 10b for interconnection with the input end 20a of the core-only solid optical fiber probe tip 20. Likewise, the core-only solid optical fiber probe tip 20 is configured with an output end 20b for interconnection with the input end 12a of output hollow fiber waveguide 12, which also includes an output end 12b for sending radiation to a detector system for interpretation of the output radiation.

As illustrated here, the ATR tip can be coupled to the hollow waveguides 10 and 12 without the use of additional optics or mechanical positioning devices.

As such, a distinguishing characteristic of the present invention from the prior art will be understood such that an outside diameter of the core-only solid optical fiber probe tip 20 and an inside diameter of each one of the input hollow fiber waveguide 10 and the output hollow fiber waveguide 12 is such that the interconnection between each one of the hollow fiber waveguides 10 and 12 and the core-only solid optical fiber probe tip 20 is by means of inserting the input end of the core-only solid optical fiber probe tip 20a into the output end 10b of the input hollow fiber waveguide 10 and inserting the output end 20b of the core-only solid optical fiber probe tip 20 into the input end 12a of the output hollow fiber waveguide 12, such that the core-only solid optical fiber probe tip 20 is held in the input and output hollow fiber waveguides 10 and 12 by means of friction. More specifically, the hollow waveguides may be configured with an inside diameter of about 0.75-1.0 mm.

It should be noted that such friction retention renders the interconnection between the core-only solid optical fiber probe tip 20 and the input and output hollow fiber waveguides 10 and 12 easily releasable, thereby enabling insertion of a new core-only solid optical fiber probe tip 20 for each use.

It will be appreciated that the interconnection between the core-only solid optical fiber probe tip 20 is held in the input and output hollow fiber waveguides 10 and 12 may be enhanced by the use of a coupling agent 30 which will transmit thermal IR radiation with high efficiency but avoid any chemical reaction between the inner coating of the hollow fiber and the solid optical fiber core components. To explain further, it is preferable that the surface area of the solid optical fiber core 20 that comes in physical contact with hollow fiber, and more specifically the inner coating of the hollow fiber waveguide, may be coated with a thin layer such as, but not limited to, a few microns of a coupling-coating layer of noble metal such as, but not limited to gold (Au). Optionally, other coating materials such as, but not limited to, graphene which will transmit thermal IR energy with maximal energy transfer efficiency but will avoid chemical reaction between the inner coating of the hollow fiber and solid optical fiber core during contact.

It will be further appreciated that the ATR tips 20 can be configured in a variety of different forms or shapes such as, but not limited to, U-shaped (as illustrated herein), loop, flat form, lens-like form, hexagon and triangle for example.

A core-only silver halide solid fiber can be used as the ATR element. The polycrystalline silver halide (e.g. $AgCl_xBr_{1-x}$) fibers are among the most useful ones for applications in the mid-IR. These fibers have a wide transparency range (~2-20 um wavelength), they are non-toxic, flexible and insoluble in water. Silver halide fibers have diameters in the range of 0.5 to 1 mm and length of several meters. It will be appreciated that the solid optical fiber tip may be fabricated from substantially any suitable material such as, but not limited to, zinc selenide and others.

Advances in polycrystalline silver halide optical fibers are enabling clinical applications of FTIR for tissue analyses. They operate with low optical losses (0.1-0.5 dB/m in the region of 10 um) and high flexibility (R-bending>10-100 fiber diameters) in the spectral range of 3-20 um.

Two basic types of silver halide fiber probes are the most common, and include a U-loop-tipped fiber and a diamond-tipped fiber.

In the ATR configuration, the fiber tip is formed, into a loop so that there is no physical interruption of the light path between the light delivery (input) and collection (output) fibers To create the ATR core-only solid optical fiber probe tip 20, the cladding of the solid optical fiber is removed such that the core may be placed in direct contact with the sample when in use. When light experiences total internal reflection at the core-sample interface, some of the energy of the light waves in the core of the fiber penetrate into the sample for a very short distance. The energy flow of this evanescent wave is parallel to the surface of the core and in the same direction as the main flow of energy within the core.

Any materials which absorb the particular wavelength of radiation will take energy out of the evanescent wave, thereby modifying the output radiation of the ATR probe 2.

With the proposed coupling arrangement the need to use large size optical elements (like expensive Diamond ATR elements) is eliminated. As a result, the probe diameter can be substantially reduced together with the price, while the resulting probe will be more flexible and can be used, for example, for endoscopy.

It will be understood that the radiation source used with the ATR probe 2 of the present invention may be, but is not limited to, optical characterization systems including one or more light sources, lasers and the like. It will be further understood that detectors used with the ATR probe 2 of the present invention may be, but are not limited to, spectrometer based on diffraction grating, Fourier Transform spectrometer/interferometer or spectral filter with a related photo-element or array of detectors.

In general, hollow waveguides, which are particularly useful for transmitting electromagnetic radiation (in the UV, visible, and IR spectral range), are made from glass or plastic tubes whose core consists of air. In some of these waveguides the inner surface is coated with a metallic layer, which is frequently coated with another layer of dielectric material.

Figure 2B:
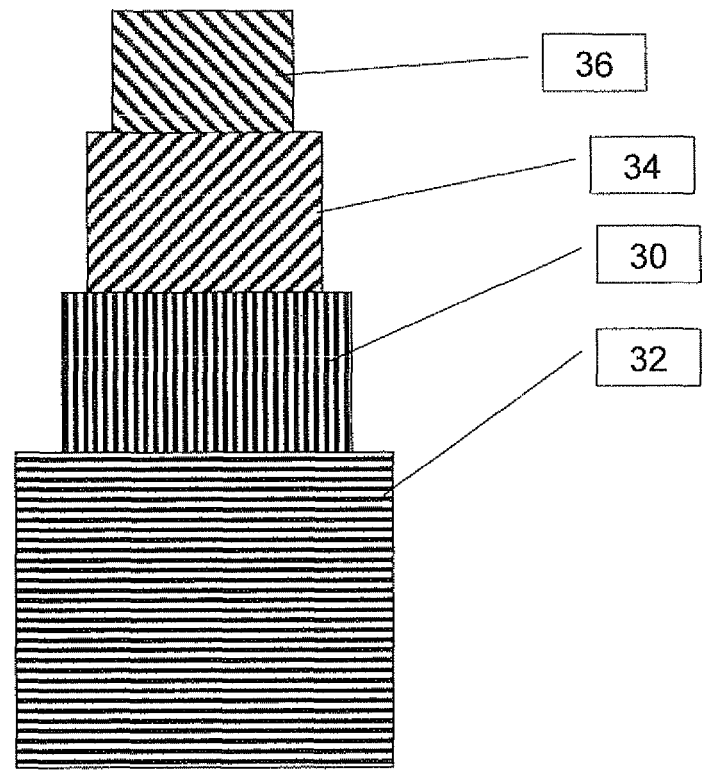

FIGS. 2A and 2B illustrate a preferred configuration of the input and output hollow fiber waveguides 10 and 12 in which the silica tube base 30 has a an acrylate outer coating 32, a silver film interior coating 34 that is in turn coated by a silver iodide film 36 as the dielectric coating. It will be readily understood that the core of hollow fiber waveguides, being hallow, are filled with air.

Figure 3:
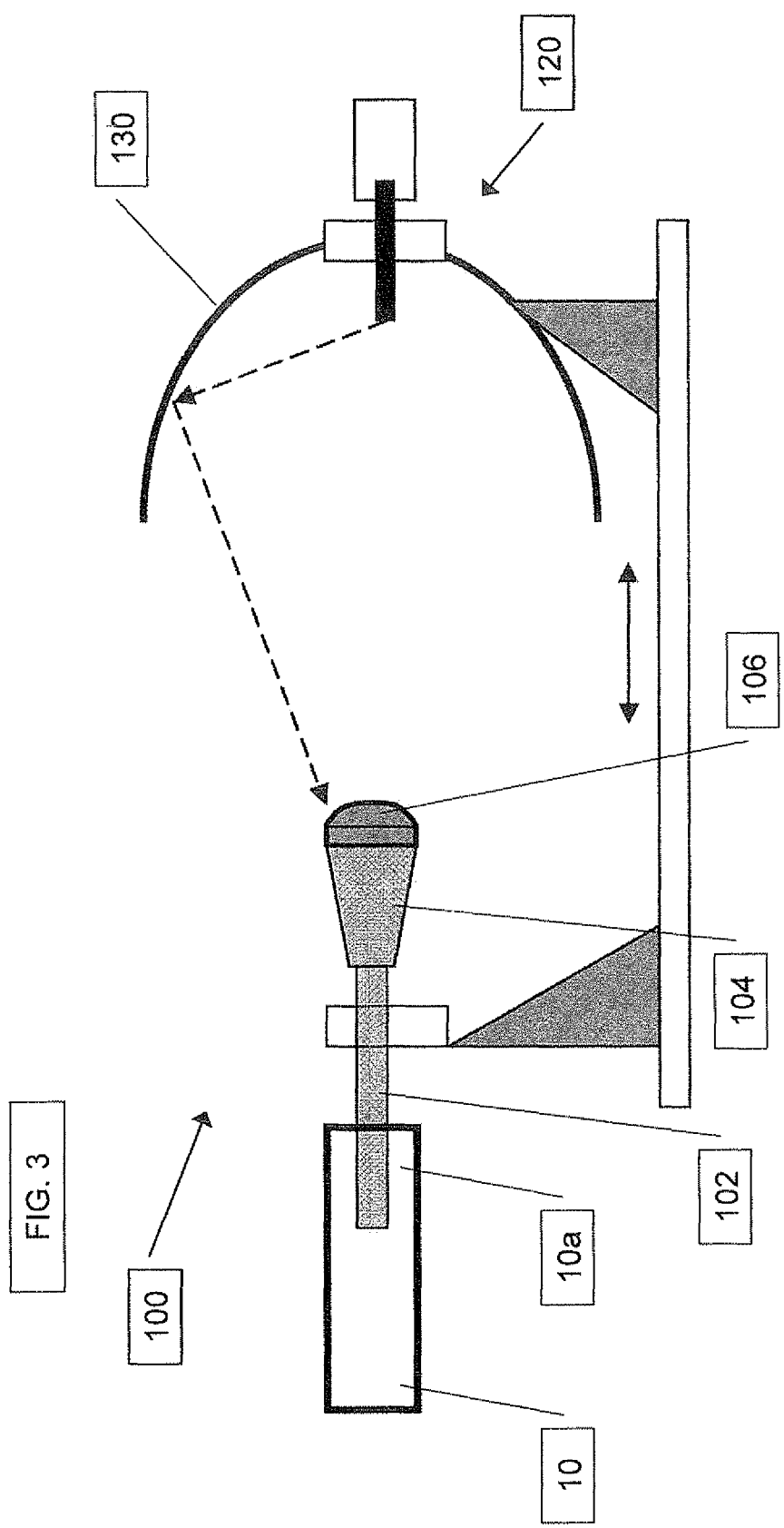
FIG. 3 is a side section of a first preferred embodiment of a radiation source constructed and operational according to the teaching of the present invention, shown here with an ellipsoidal reflector.
Figure 4:
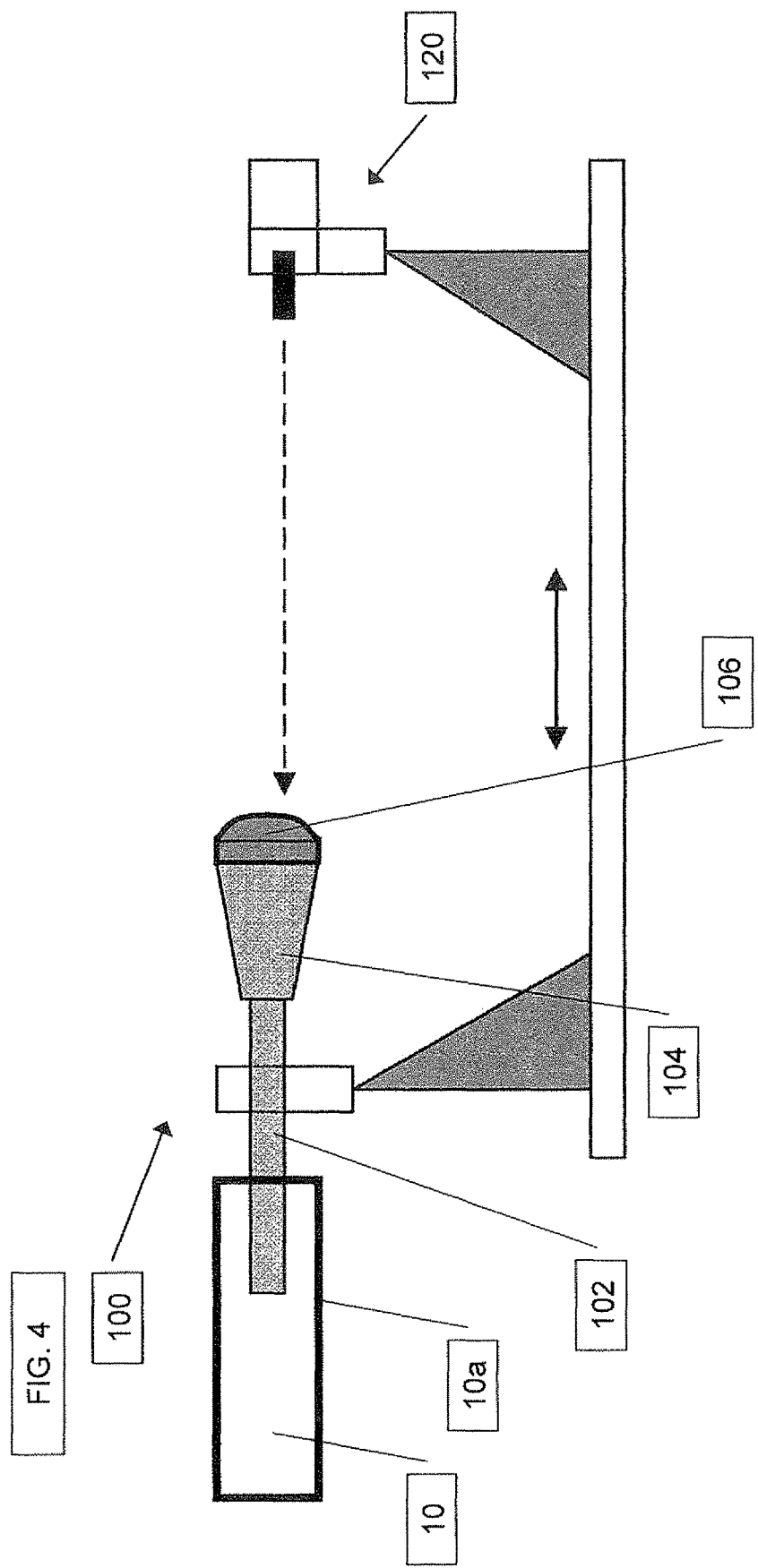
FIG. 4 is a side section of a second preferred embodiment of a radiation source constructed and operational according to the teaching of the present invention.

As illustrated in FIGS. 3 and 4, in one embodiment of the present invention, in order to increase the amount of input energy and to improve signal-to-noise ratio within the ATR probe 2, the input end 10a of the input hollow fiber waveguide 10 is connected to an inwardly tapered (horn-shaped) solid fiber input collector element 100 by directly inserting the pigtail end 102 at the tapered end of the fiber into the input end 10a of the input hollow fiber waveguide 10. It will be understood that the pigtail end 102 of the tapered solid fiber input collector element 100, may be coated with a coupling material which will transmit thermal IR radiation with high efficiency but avoid any chemical reaction between the inner coating of the hollow fiber and the pigtail end 102 of the inwardly tapered (horn-shaped) solid fiber input collector element 100.

As illustrated in FIG. 3, the radiation source 120 may include an ellipsoidal reflector 130 to further increase the radiation energy delivered into the inwardly tapered solid fiber input collector element 100. Alternatively, as seen in FIG. 4, the radiation energy may be delivered directly into the inwardly tapered solid fiber input collector element 100 from the radiation source 120 without using the ellipsoidal reflector.

Figure 5:
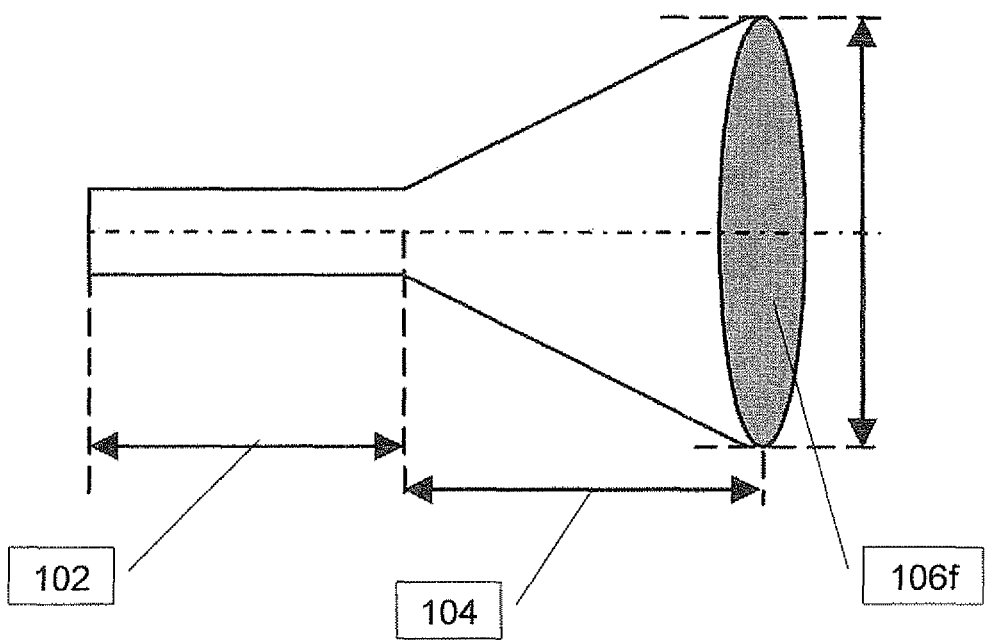
FIG. 5 is a side section of a first preferred embodiment of an inwardly tapered solid fiber input radiation collector element constructed and operational according to the teaching of the present invention, shown here with a flat face.
Figure 6:
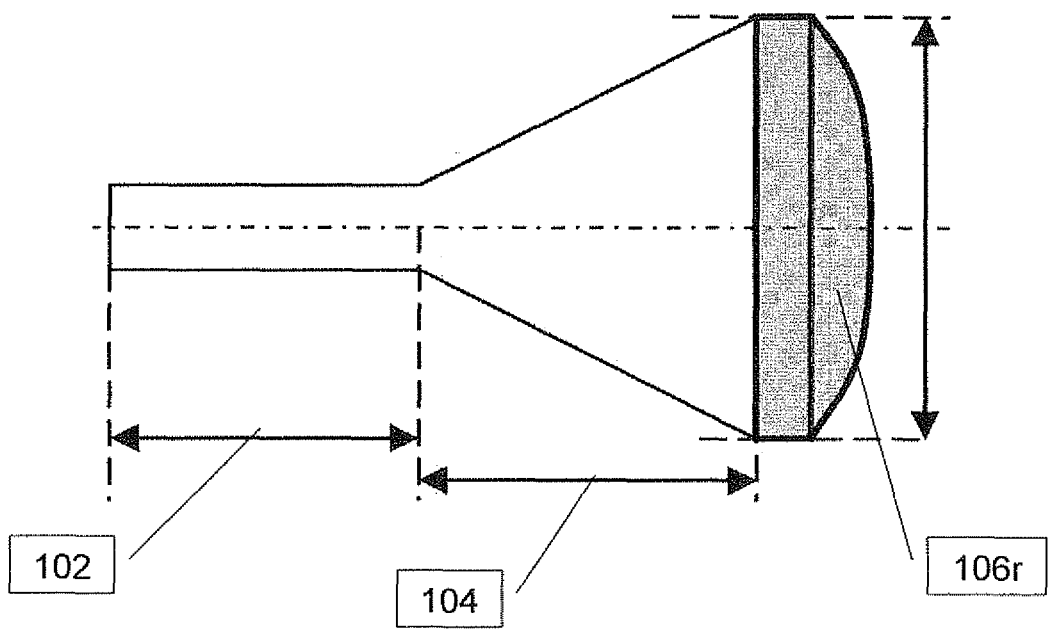
FIG. 6 is a side section of a second preferred embodiment of an inwardly tapered solid fiber input radiation collector element constructed and operational according to the teaching of the present invention, shown here with a lens face.

FIGS. 5 and 6 illustrate that the input face of inwardly tapered solid fiber input collector element 100 can have different configurations such as, but not limited to, flat 106l, spherical and rounded lens 106r for example.

Figure 7:
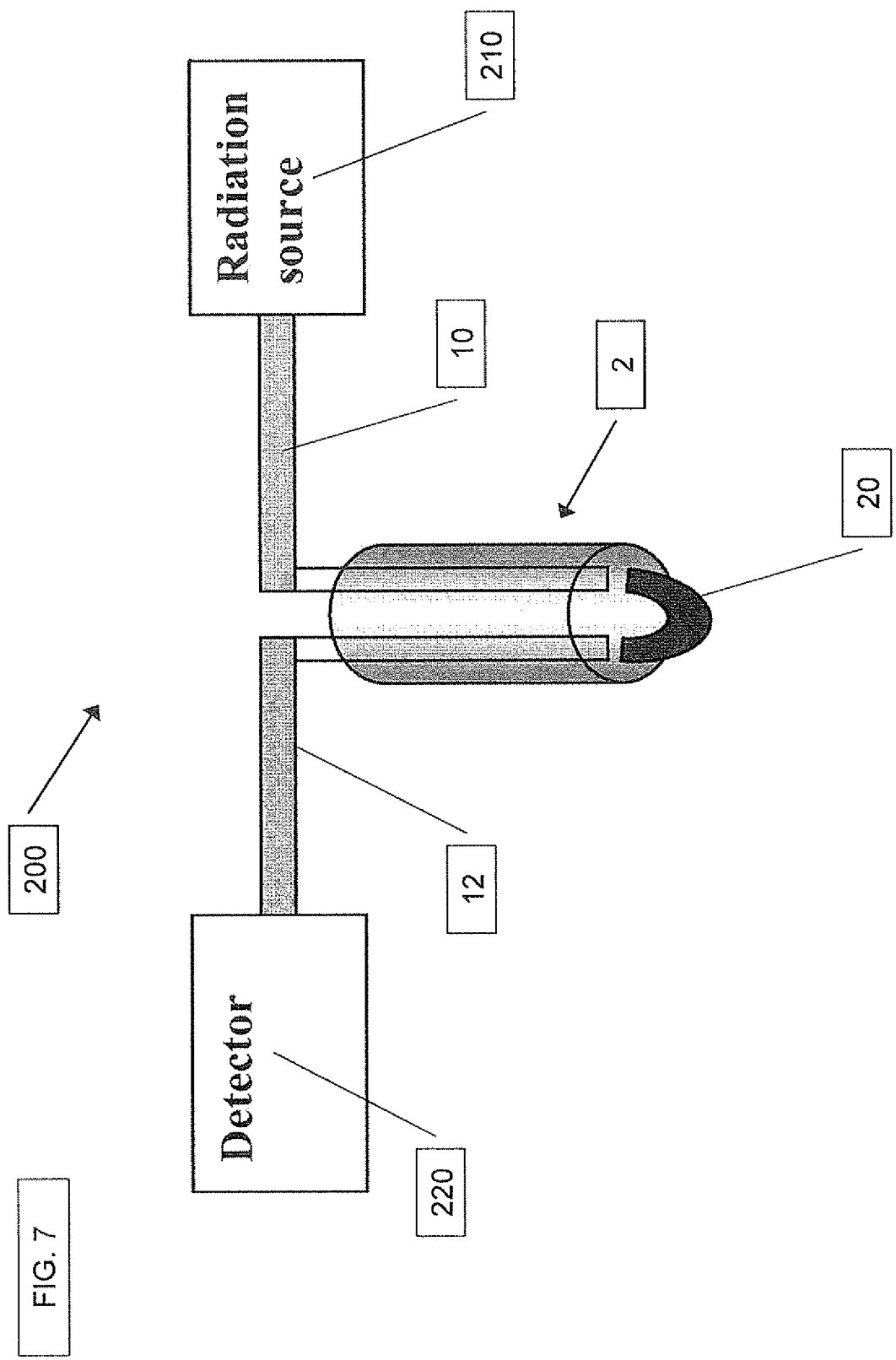
FIG. 7 is a block diagram representing a system for use with a hybrid ATR fiber optic probe device of the present invention.

FIG. 7 illustrates a full system 200 for use with ATR probe 2, in which the input hollow fiber waveguide 10 is connected to a radiation source 210 and the output hollow fiber waveguide 12 is connecter to a detector 220.

It will be readily appreciated that the system illustrated in the block diagram of FIG. 7 may be implemented for use with an endoscope.

The hybrid ATR probe is easily inserted in the working channel of the endoscope during examination. In one embodiment, the configuration may include the forceps are similar to those typically used by gastroenterologists.

During a traditional colonoscopy, endoscopic or laparoscopy procedures the physician inserts an endoscope into the body orifice or abdominal incisions and maneuvers the end of the scope to areas of interest. There is typically a video camera on the end of the endoscope so that the physician can examine tissue close to the end of the endoscope. Endoscopes have a "working" channel, essentially a small hole which runs the length of the endoscope through which a physician can insert various tools and/or biopsy forceps. Such working channels may be internal or external working channels. It is within this spare channel the ATR probe or ATR probe and forceps may be inserted. The ATR probe can be installed in an endoscope such that the solid optical fiber tip can be combined within the distal part of the endoscope next to the camera while the hollow fibers wave guide are placed within or along the endoscope.

Additionally, the ATR probe 2 may be associated with a tool for dehydration and drying tissue. Further, a system for introducing cleaning fluid may also be associated with the ATR probe for cleaning the core-only solid optical fiber probe tip 20.

It will be understood that the dehydration tool may be part of the device to which the ends of hollow fiber waveguide are connected. Such ATR probe configuration can be used for in-vitro tissue diagnostics.

FIG. 8 illustrates a portable miniaturized embodiment of a full system 300 for use with ATR probe 2, in which the input hollow fiber waveguide 10, the output hollow fiber waveguide 12, radiation source 310 and connecter to a detector 320 are deployed in a pen style housing. It will be appreciated that the pen style housing may also include a means for transmitting data to a analyzing system such as, but not limited to, a Fourier Transform spectrometer. Such data transfer may be by way of a cable connection or wirelessly using known wireless communication protocols.

It will be appreciated that the above descriptions are intended only to serve as examples and that many other embodiments are possible within the spirit and the scope of the present invention.

What is claimed is:

1. A hybrid Attenuated Total Reflection fiber optic probe device comprising:
   (a) a radiation source;
   (b) a detecting system;
   (c) a core-only solid optical fiber probe tip having an input end and an output end;
   (d) an input hollow fiber waveguide configured for association with said radiation source at a first end and interconnection with said input end of said core-only solid optical fiber probe tip at a second end;
   (e) an output hollow fiber waveguide configured for interconnection with said output end of said core-only solid optical fiber probe tip at a first end and association with said detection system at a second end;
   (f) an inwardly tapered solid fiber input radiation collector element configured at a tapered end for interconnection with said second end of said output hollow fiber waveguide so as to receive radiation from said radiation source;
   wherein an outside diameter of said core-only solid optical fiber probe tip and an inside diameter of each one of said input hollow fiber waveguide and said output hollow fiber waveguide is such that said interconnection between each one of said input hollow fiber waveguide and said output hollow fiber waveguide and said core-only solid optical fiber probe tip is by means of inserting said input end of said core-only solid optical fiber probe tip into said second end of said input hollow fiber waveguide and inserting said output end of said core-only solid optical fiber probe tip into said first end of said output hollow fiber waveguide, such that said core-only solid optical fiber probe tip is held in said input and output hollow fiber waveguides by means of friction, and wherein an outside diameter of a portion of said inwardly tapered solid fiber input radiation collector element and an inside diameter of said second end of said output hollow fiber waveguide is such that said tapered end of said inwardly tapered solid fiber input radiation collector element is held in said end of said second end of said output hollow fiber waveguide by means of friction.

2. The hybrid Attenuated Total Reflection fiber optic probe device of claim 1, wherein said interconnection between said core-only solid optical fiber probe tip and said input and output hollow fiber waveguides is a releasable interconnection.

3. The hybrid Attenuated Total Reflection fiber optic probe device of claim 1, wherein said interconnection between said core-only solid optical fiber probe tip and said input and output hollow fiber waveguides includes a coupling agent on a surface area of contact between said core-only solid optical fiber probe tip and said input and output hollow fiber waveguides.

4. The hybrid Attenuated Total Reflection fiber optic probe device of claim 3, wherein said coupling agent being a layer of one of: a noble metal and graphene.

5. The hybrid Attenuated Total Reflection fiber optic probe device of claim 1, wherein said inwardly tapered solid fiber input radiation collector element includes:
　(a) an input face;
　(b) an inwardly tapered section extending from said input face to;
　(c) a output connection section configured for interconnection with the hollow fiber waveguide and having a substantially constant diameter that is smaller than a diameter of said input face;
wherein said diameter of said connection section and an inside diameter of the hollow fiber waveguide is such that said inwardly tapered solid fiber input radiation collector element is held in the end of the hollow fiber waveguide by means of friction.

6. The hybrid Attenuated Total Reflection fiber optic probe device of claim 5, wherein said input face is flat.

7. The inwardly tapered solid fiber input radiation collector element of claim 3, wherein said input face is lens shaped.

8. A method for attaching a solid optical fiber element to a hollow fiber waveguide, the method comprising:
　(a) providing a solid optical fiber element having at least one of an input end and an output end;
　(b) providing at least one hollow fiber waveguide configured for interconnection with one of said input end and output end of said solid optical fiber element at an end;
　(c) coating a surface area of contact between said solid optical fiber element and said at least one hollow fiber waveguide with a coupling agent implemented as a layer of one of: a noble metal and graphene; and
　(d) inserting at least one of said input end and an output end at least partially into said end of said hollow fiber waveguide;
wherein an outside diameter of said solid optical fiber element and an inside diameter of said hollow fiber waveguide is such that said solid optical fiber element is held in said end of said hollow fiber waveguide by means of friction.

9. The method of claim 8, wherein said solid optical fiber element is implemented as a core-only solid optical fiber probe tip having an input end and an output end, said at least one hollow fiber waveguide is implemented as two hollow fiber waveguides configured as an input hollow fiber waveguide and an output hollow fiber waveguide and said inserting includes inserting said input end of said core-only solid optical fiber probe tip at least partially into said input hollow fiber waveguide and inserting said output end of said core-only solid optical fiber probe tip at least partially into said output hollow fiber waveguide.

10. The method of claim 8, wherein said solid optical fiber element is implemented as an inwardly tapered solid fiber input radiation collector element having at least an output connection section.

* * * * *